(12) United States Patent
Gordan et al.

(10) Patent No.: US 7,803,358 B2
(45) Date of Patent: Sep. 28, 2010

(54) MQ AND T-PROPYL SILOXANE RESINS COMPOSITIONS

(75) Inventors: Glenn Viaplana Gordan, Midland, MI (US); Randall Gene Schmidt, Midland, MI (US); Lori Ann Stark-Kasley, Midland, MI (US); Gary Michael Wieber, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 121 days.

(21) Appl. No.: 10/586,010

(22) PCT Filed: Jan. 20, 2005

(86) PCT No.: PCT/US2005/003106

§ 371 (c)(1),
(2), (4) Date: Jul. 12, 2006

(87) PCT Pub. No.: WO2005/075567

PCT Pub. Date: Aug. 18, 2005

(65) Prior Publication Data

US 2007/0166271 A1 Jul. 19, 2007

Related U.S. Application Data

(60) Provisional application No. 60/541,001, filed on Feb. 2, 2004.

(51) Int. Cl.
| | | |
|---|---|---|
| *A61K 8/58* | (2006.01) | |
| *A61K 8/00* | (2006.01) | |
| *A61K 8/18* | (2006.01) | |
| *A61K 8/72* | (2006.01) | |
| *A61Q 5/12* | (2006.01) | |
| *A61Q 5/00* | (2006.01) | |
| *A61Q 9/00* | (2006.01) | |
| *A61Q 7/00* | (2006.01) | |

(52) U.S. Cl. .............. 424/70.121; 424/70.11; 424/70.12; 424/70.1

(58) Field of Classification Search .......... 424/64, 424/70.1, 70.12, 70.11, 70.121; 524/500
See application file for complete search history.

(56) References Cited

U.S. PATENT DOCUMENTS

| | | | |
|---|---|---|---|
| 2,814,601 A | 11/1957 | Currie et al. | |
| 2,857,356 A | 10/1958 | Goodwin | |
| 5,063,254 A | 11/1991 | Nakos | |
| 5,075,103 A | 12/1991 | Halloran et al. | |
| 5,085,859 A | 2/1992 | Halloran et al. | |
| 5,330,747 A | 7/1994 | Krzysik | |
| 5,733,537 A | 3/1998 | Halloran et al. | |
| 5,837,223 A | 11/1998 | Barone et al. | |
| 6,036,947 A | 3/2000 | Barone et al. | |
| 6,071,503 A | 6/2000 | Drechsler et al. | |
| 6,074,654 A | 6/2000 | Drechsler et al. | |
| 6,139,823 A | 10/2000 | Drechsler et al. | |
| 6,340,466 B1 | 1/2002 | Drechsler et al. | |
| 6,406,683 B1 | 6/2002 | Drechsler et al. | |
| 2002/0031488 A1 | 3/2002 | Kanji et al. | |
| 2002/0058054 A1 | 5/2002 | Arnaud | |
| 2002/0114773 A1* | 8/2002 | Kanji et al. | ............... 424/70.21 |
| 2002/0187170 A1 | 12/2002 | Pavlin | |
| 2003/0236387 A1 | 12/2003 | Pavlin | |
| 2004/0180011 A1* | 9/2004 | Schlosser | ..................... 424/64 |

FOREIGN PATENT DOCUMENTS

| | | |
|---|---|---|
| EP | 0 336 633 | 8/1996 |
| GB | 2 294 392 | 5/1996 |
| GB | 2 319 527 | 5/1998 |
| JP | 61158910 | 7/1986 |
| JP | 4139114 | 5/1992 |
| JP | 1994-72085 | 9/1994 |
| JP | 7330536 | 12/1995 |
| KR | 2002054603 | 7/2002 |
| WO | WO 97/17058 | 5/1997 |
| WO | WO 97/17059 | 5/1997 |
| WO | WO 02/089760 | 11/2002 |
| WO | WO 2005/075542 | 8/2005 |

* cited by examiner

*Primary Examiner*—Mark Eashoo
*Assistant Examiner*—Angela C Scott
(74) *Attorney, Agent, or Firm*—Patricia M. Scaduto

(57) ABSTRACT

Siloxane resin compositions obtained by mixing a MQ siloxane resin with a propyl silsesquioxane resin are disclosed. These siloxane resins are useful in a variety of personal, household, automotive and medical care applications, and in particular, as a resin additive in pigmented cosmetic formulations.

5 Claims, 2 Drawing Sheets

MQ AND T-PROPYL SILOXANE RESINS COMPOSITIONS

CROSS REFERENCE TO RELATED APPLICATIONS

This application is a U.S. national stage filing under 35 U.S.C. §371 of PCT Application No. PCT/US05/003106 filed on 20 Jan. 2005, currently pending, which claims the benefit of U.S. Provisional Patent Application No. 60/541,001 filed 2 Feb. 2004 under 35 U.S.C. §119(e). PCT Application No. PCT/US05/003106 and U.S. Provisional Patent Application No. 60/541,001 are hereby incorporated by reference.

FIELD OF THE INVENTION

The present invention provides siloxane resin compositions obtained by mixing a MQ siloxane resin with a propyl silsesquioxane resin. The siloxane resin compositions of the present invention are useful in a variety of personal, household, automotive and medical care applications, and in particular, as a resin additive in pigmented cosmetic formulations.

BACKGROUND OF THE INVENTION

Siloxane resins of the general formula $R_n SiO_{(4-n)/2}$, where R is an alkyl group and n is generally less than 1.8, are an important family of silicone polymers because of their utility in many commercial applications such as adhesive compositions and coatings applications. One particular subclass of siloxane resins, known as MQ resins (since they comprise primarily of "M" units of the general formula $R_3SiO_{1/2}$ and "Q" units of the general formula $SiO_2$), have found utility in cosmetic formulations. In particular MQ resins are commonly used in "extended wear" or "transfer resistant" cosmetic formulations. In these formulations, MQ resins enhance the substantivity of the pigments or other formulation actives to skin after application creating a longer lasting, and hence extended wear product.

Representative examples of transfer resistant cosmetic compositions using MQ resins are found in U.S. Pat. Nos. 6,071,503, 6,074,654, 6,139,823, 6,340,466, WO 97/17058, and WO 97/17059 which disclose compositions comprising the combination of organosiloxane resins and fluid diorganosiloxane resins with a volatile carrier.

U.S. Pat. No. 5,330,747 teaches cosmetics with enhanced durability using a film forming agent from a pressure sensitive adhesive composition comprising a trimethylsilyl endblocked resinous copolymer, a silanol endblocked polydiorganosiloxane fluid, and a phenyl containing polysiloxane fluid.

U.S. Pat. Nos. 5,075,103 and 5,733,537 teach a hair treating method for imparting curl retention to hair in which at least one film-forming ingredient is applied to the hair. The improvement utilizes as the film-forming ingredient an organosilicon compound which is a nonpolar silsesquioxane.

U.S. Pat. No. 5,800,816 discloses cosmetic compositions having improved transfer resistance comprising: a) from about 0.1-60% by weight of trimethylated silica, b) from about 0.1-60% by weight of a volatile solvent having a viscosity of 0.5 to 100 centipoise at 25° C., c) 0.1-60% by weight of a nonvolatile oil having a viscosity of 200 to 1,000,000 centipoise at 25° C., d) 0.1-80% of a cosmetically acceptable carrier.

U.S. Pat. Nos. 5,837,223 and 6,036,947 teach transfer resistant high luster cosmetic stick compositions comprising, by weight of the total composition: a) 10-70% of a volatile solvent having a viscosity of 0.5 to 20 centipoise at 25.degree. C., b) 0.5-40% of a guerbet ester, and c) 0.1-20% of a siloxy-silicate polymer.

GB 2,319,527 discloses fragrance releasing non-volatile polysiloxanes based on a high molecular weight polydiorganosiloxane compounds where at least one or more of the organic substituents of the polymer is a radical derived from a fragrant alcohol.

Japanese examined patent publication 1994-72085 teaches makeup cosmetic compositions having improved water resistance and durability containing an organic silicone resin, a volatile silicone oil, and a make up powder.

While the use of MQ resins in cosmetics have led to formulations having extended wear or transfer resistance, a need exists to alter the properties of the siloxane resins used in such formulations. In particular, films of MQ resins used in these formulations can have a matte finish and are brittle. Thus, there is a need for improved siloxane resins that offer at least comparable extended wear and transfer resistance properties of the MQ resins presently used in cosmetic formulations, but having improved gloss (i.e. non-matte), are still non-tacky, and are more flexible. Furthermore, there is a need for resins in hair care formulations that improve the curl retention properties of hair following treatment.

The present inventors have discovered improved siloxane resin compositions by forming compatible blends of propyl silsesquioxane resins with MQ resins. The resulting siloxane resin compositions have improved physical properties. In particular, cosmetic formulations containing the present siloxane resin compositions have improved gloss and are more flexible than MQ resins alone, while maintaining their long lasting or wear characteristics.

SUMMARY OF THE INVENTION

This invention provides a siloxane resin composition obtained by mixing:

A) a MQ resin comprising at least 80 mole % of siloxy units selected from
   $(R^1_3SiO_{1/2})_a$ and $(SiO_{4/2})_b$ units, where $R^1$ is independently an alkyl group having from 1 to 8 carbon atoms, an aryl group, a carbinol group, or an amino group, with the proviso that at least 95 mole % of the $R^1$ groups are alkyl groups, a and b has a value greater than zero, and the ratio of a/b is 0.5 to 1.5;

B) a propyl silsesquioxane resin comprising at least 80 mole % $R^3SiO_{3/2}$ units,
   where $R^3$ is independently an alkyl group having from 1 to 8 carbon atoms, an aryl group, a carbinol group, or an amino group,
   with the proviso that at least 40 mole % of the $R^3$ groups are propyl, and optionally;

C) a volatile siloxane or organic solvent,
   wherein the weight ratio of component A to B is from 1:99 to 99:1.

The siloxane resins are useful in a variety of personal, household, or medical care compositions. In particular, the siloxane resin compositions provide glossy, non-tacky films that can be used to enhance the substantivity of color cosmetic formulations. The siloxane resin compositions can also be used in hair care formulations to enhance curl retention properties. The siloxane resin compositions can also enhance the feel of treated hair, providing a softer feel compared to other siloxane resin. Thus, the present invention provides personal, household, automotive, or medical care compositions comprising the siloxane resin compositions described herein.

DETAILED DESCRIPTION OF THE INVENTION

Figure 1:
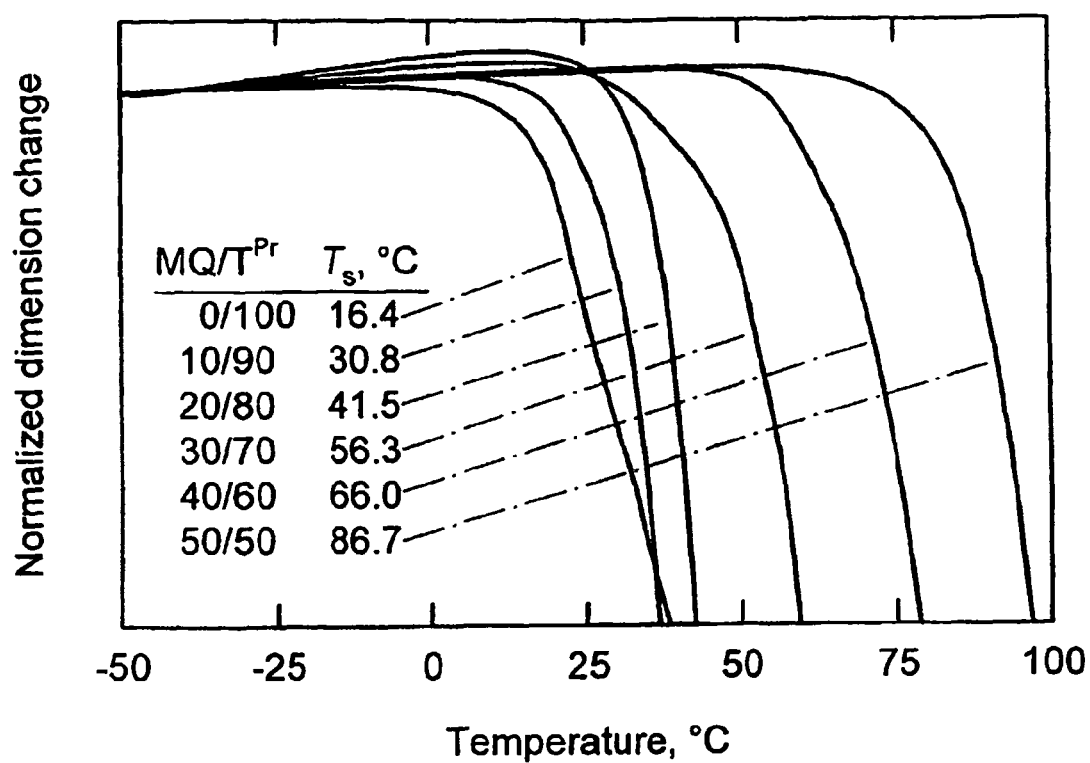
FIG. 1 shows the normalized dimension change of MQ/T (Pr) blends versus temperature.

Component A) is a MQ resin comprising at least 80 mole % of siloxy units selected from $(R^1{}_3SiO_{1/2})_a$ and $(SiO_{4/2})_b$ units, where $R^1$ is an alkyl group having from 1 to 8 carbon atoms, an aryl group, a carbinol group, or an amino group, with the proviso that at least 95 mole % of the $R^1$ groups are alkyl groups, a and b has a value greater than zero, and the ratio of a/b is 0.5 to 1.5.

The $R^1$ units of the MQ resin are independently an alkyl group having from 1 to 8 carbon atoms, an aryl group, a carbinol group, or an amino group. The alkyl groups are illustrated by methyl, ethyl, propyl, butyl, pentyl, hexyl, and octyl. The aryl groups are illustrated by phenyl, naphthyl, benzyl, tolyl, xylyl, xenyl, methylphenyl, 2-phenylethyl, 2-phenyl-2-methylethyl, chlorophenyl, bromophenyl and fluorophenyl with the aryl group typically being phenyl.

For the purposes of this invention a "carbinol group" is defined as any group containing at least one carbon-bonded hydroxyl (COH) radical. Thus the carbinol groups may contain more than one COH radical such as for example

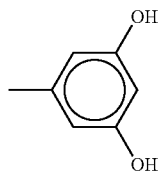

The carbinol group if free of aryl groups has at least 3 carbon atoms, or an aryl-containing carbinol group having at least 6 carbon atoms, The carbinol group free of aryl groups having at least 3 carbon atoms is illustrated by groups having the formula $R^4OH$ wherein $R^4$ is a divalent hydrocarbon radical having at least 3 carbon atoms or divalent hydrocarbonoxy radical having at least 3 carbon atoms. The group $R^4$ is illustrated by alkylene radicals such as —$(CH_2)_x$— where x has a value of 3 to 10, —$CH_2CH(CH_3)$—, —$CH_2CH(CH_3)CH_2$—, —$CH_2CH_2CH(CH_2CH_3)CH_2CH_2CH_2$—, and —$OCH(CH_3)(CH_2)_x$— wherein x has a value of 1 to 10.

The aryl-containing carbinol group having at least 6 carbon atoms is illustrated by groups having the formula $R^5OH$ wherein $R^5$ is an arylene radical such as —$(CH_2)_xC_6H_4$— wherein x has a value of 0 to 10, —$CH_2CH(CH_3)(CH_2)_x$ $C_6H_4$— wherein x has a value of 0 to 10, —$(CH_2)_xC_6H_4$ $(CH_2)_x$— wherein x has a value of 1 to 10. The aryl-containing carbinol groups typically have from 6 to 14 atoms.

The amino group is illustrated by groups having the formula —$R^6NH_2$ or —$R^6NHR^7NH_2$ wherein $R^6$ is a divalent hydrocarbon radical having at least 2 carbon atoms and $R^7$ is a divalent hydrocarbon radical having at least 2 carbon atoms. The group $R^6$ is typically an alkylene radical having from 2 to 20 carbon atoms. $R^6$ is illustrated by ethylene, propylene, —$CH_2CHCH_3$—, butylene, —$CH_2CH(CH_3)CH_2$—, pentamethylene, hexamethylene, 3-ethyl-hexamethylene, octamethylene, and decamethylene.

$R^7$ is typically an alkylene radical having from 2 to 20 carbon atoms. $R^7$ is illustrated by ethylene, propylene, —$CH_2CHCH_3$—, butylene, —$CH_2CH(CH_3)CH_2$—, pentamethylene, hexamethylene, 3-ethyl-hexarnethylene, octamethylene, and decamethylene.

Typical amino groups are —$CH_2CH_2CH_2NH_2$ and —$CH_2(CH_3)CHCH_2(H)NCH_3$, —$CH_2CH_2NHCH_2CH_2NH_2$, —$CH_2CH_2NH_2$, —$CH_2CH_2NHCH_3$, —$CH_2CH_2CH_2CH_2NH_2$, —$(CH_2CH_2NH)_3H$, and —$CH_2CH_2NHCH_2CH_2NHC_4H_9$.

Typically, $R^1$ is a methyl group.

MQ resins suitable for use as component (A), and methods for their preparation, are known in the art. For example, U.S. Pat. No. 2,814,601 to Currie et al., Nov. 26, 1957, which is hereby incorporated by reference, discloses that MQ resins can be prepared by converting a water-soluble silicate into a silicic acid monomer or silicic acid oligomer using an acid. When adequate polymerization has been achieved, the resin is end-capped with trimethylchlorosilane to yield the MQ resin. Another method for preparing MQ resins is disclosed in U.S. Pat. No. 2,857,356 to Goodwin, Oct. 21, 1958, which is hereby incorporated by reference. Goodwin discloses a method for the preparation of an MQ resin by the cohydrolysis of a mixture of an alkyl silicate and a hydrolyzable trialkylsilane organopolysiloxane with water.

The MQ resins suitable as component A) in the present invention may contain D and T units, providing that at least 80 mole %, alternatively 90 mole % of the total siloxane units are M and Q units. The MQ resins may also contain hydroxy groups. Typically, the MQ resins have a total weight % hydroxy content of 2-10 weight %, alternatively 2-5 weight %. The MQ resins can also be further "capped" wherein residual hydroxy groups are reacted with additional M groups.

Component B) is a propyl silsesquioxane resin comprising at least 80 mole % of $R^3SiO_{3/2}$ units, where $R^3$ is independently an alkyl group having from 1 to 8 carbon atoms an aryl group, a carbinol group, or an amino group, and with the proviso that at least 40 mole % of the $R^3$ groups are propyl. The propyl silsesquioxane resins are referred herein as T-propyl resins, since the majority of the siloxane units are T units of the general formula $R^3SiO_{3/2}$ where at least 40 mole %, alternatively 50 mole %, or alternatively 90 mole % of the $R^3$ groups are propyl. The $R^3$ groups are illustrated by the same structures as described above for $R^1$ groups.

Silsesquioxane resins are well known in the art and are typically prepared by hydrolyzing an organosilane having three hydrolyzable groups on the silicon atom, such as a halogen or alkoxy group. Thus, component (B) can be obtained by hydrolyzing propyltrimethoxysilane, propyltriethoxysilane, propyltripropoxysilane, or by co-hydrolyzing the aforementioned propylalkoxysilanes with various alkoxysilanes. Examples of these alkoxysilanes include methyltrimethoxysilane, methyltriethoxysilane, methyltriisopropoxysilane, dimethyldimethoxysilane, and phenyltrimethoxysilane. Propyltrichlorosilane can also be hydrolyzed alone, or in the presence of alcohol. In this case, co-hydrolyzation can be carried out by adding methyltrichlorosilane, dimethyldichlorosilane, phenyltrichlorosilane, or similar chlorosilanes and methyltrimethoxysilane, methyltriethoxysilane, methyltriisopropoxysilane, or similar methylalkoxysilane. Alcohols suitable for these purposes include methanol, ethanol, n-propyl alcohol, isopropyl alcohol, butanol, methoxy ethanol, ethoxy ethanol, or similar alcohols. Examples of hydrocarbon-type solvents which can also be concurrently used include toluene, xylene, or similar aromatic hydrocarbons; hexane, heptane, isooctane, or similar linear or partially branched saturated hydrocarbons; and cyclohexane, or similar aliphatic hydrocarbons.

The T-propyl resins suitable as component B) in the present invention may contain M, D, and Q units, providing that at least 80 mole %, alternatively 90 mole % of the total siloxane units are T units. The T-propyl resins may also contain hydroxy and/or alkoxy groups. Typically, the T-propyl resins have a total weight % hydroxy content of 2-10 weight % and a total weight % alkoxy content of up to 20 weight %, alternatively 6-8 weight % hydroxy content and up to 10 weight % alkoxy content.

A volatile siloxane or organic solvent can be included as optional component C) when mixing components A) and B). Any volatile siloxane or organic solvent can be selected providing components A) and B) are miscible with the solvent.

The volatile siloxane solvent can be a cyclic polysiloxane, a linear polysiloxane, or mixtures thereof. Some representative volatile linear polysiloxanes are hexamethyldisiloxane, octamethyltrisiloxane, decamethyltetrasiloxane, tetradecamethylhexasiloxane, and hexadecamethylheptasiloxane. Some representative volatile cyclic polysiloxanes are hexamethylcyclotrisiloxane, octamethylcyclotetrasiloxane, decamethylcyclopentasiloxane, and dodecamethylcyclohexasiloxane. The organic solvent can be an alcohol such as methanol, ethanol, isopropanol, butanol, or n-propanol, a ketone such as acetone, methylethyl ketone, or methyl isobutyl ketone; an aromatic hydrocarbon such as benzene, toluene, or xylene; an aliphatic hydrocarbon such as heptane, hexane, octane, or isododecane; a glycol ether such as propylene glycol methyl ether, dipropylene glycol methyl ether, propylene glycol n-butyl ether, propylene glycol n-propyl ether, or ethylene glycol n-butyl ether, a halogenated hydrocarbon such as dichloromethane, 1,1,1-trichloroethane or methylene chloride, chloroform, dimethyl sulfoxide, dimethyl formamide, acetonitrile, tetrahydrofuran, white spirits, mineral spirits, or naphtha, or an ester.

There are no special requirements or conditions needed for effecting the mixing of components A) and B). Thus, any method in the art known to effect mixing of such compositions can be used. Components A) and B) can be optionally contained in a solvent, as described supra as component C). The mixing can be conducted in a batch, semi-continuous, or continuous process.

The weight ratio of component A) to component B) (i.e. A/B) in the mixture can vary from 99:1 to 1:99, alternatively 85:15 to 15:85.

The siloxane resin compositions of the present invention are useful in a variety of personal, household, automotive, or medical care applications. In particular, the siloxane resin compositions of the present invention provide glossy, non-tacky films that can be used to enhance the substantivity of color cosmetic formulations. The siloxane resin compositions can also be used as additives in hair care formulations to enhance curl retention properties. Thus, the present invention provides personal, household, automotive, or medical care compositions comprising the siloxane resins described herein.

EXAMPLES

The following examples are presented to further illustrate the compositions and methods of this invention, but are not to be construed as limiting the invention. All parts and percentages in the examples are on a weight basis and all measurements were obtained at about 23° C., unless indicated to the contrary.

Materials

MQ Resin=a MQ resin having the formula $M_{0.43}Q_{0.57}$ and $M_n$=3230 dissolved in xylenes a 70.8% solids. The MQ resin was prepared according to techniques taught by Daudt in U.S. Pat. No. 2,676,182.

T propyl resin=propyl silsesquioxane resin at 74.8 wt % in toluene. The propyl silsesquioxane resin was prepared from the hydrolysis of propyl trichlorosilane.

Phenyl silsesquioxane resin=a phenyl silsesquioxane solid flake resin at 100 wt % solids prepared from the hydrolysis of phenyl trichlorosilane.

Examples 1-6

Solutions of MQ resin and T propyl resin were mixed in a glass bottle by shaking or putting on a mixing wheel. An aliquot of each mixture was poured into a 2-inch diameter aluminum weighing dish and heated in a forced air oven for one hour at 110° C. followed by one hour and 25 minutes at 140° C. Qualitative visual observations of clarity, brittleness and hardness were made (Table 1).

These examples demonstrate the unexpected miscibility of the MQ and T propyl resins, based on devolatilized blend clarity and the increasing hardness and brittleness trend as the MQ resin loading increased.

TABLE 1

MQ/T propyl resin blends.

| Example | MQ (g) | T propyl (g) | Aliquot (g) | Dried Sample (g) | MQ loading (wt %) | Clarity | Qualitative Brittleness | Qualitative Hardness |
|---|---|---|---|---|---|---|---|---|
| 1 | 0.00 | 13.46 | 2.0475 | 1.5361 | 0.0% | clear | Does not crack | Gummy soft solid |
| 2 | 1.40 | 12.03 | 2.0643 | 1.5415 | 9.9% | clear | Slight cracking on extreme | "Grabby" soft solid |
| 3 | 2.88 | 16.74 | 2.0840 | 1.5517 | 14.0% | clear | Cracks on moderate | Harder than #2 |
| 4 | 4.19 | 9.39 | 2.0746 | 1.5414 | 29.7% | clear | Cracks on moderate | Harder than #3 |
| 5 | 5.72 | 8.14 | 2.1066 | 1.5606 | 39.9% | clear | Cracks on slight | Harder than #4 |
| 6 | 7.11 | 6.82 | 2.0257 | 1.4968 | 49.6% | clear | Cracked upon | similar to #5 |

Figure 2:
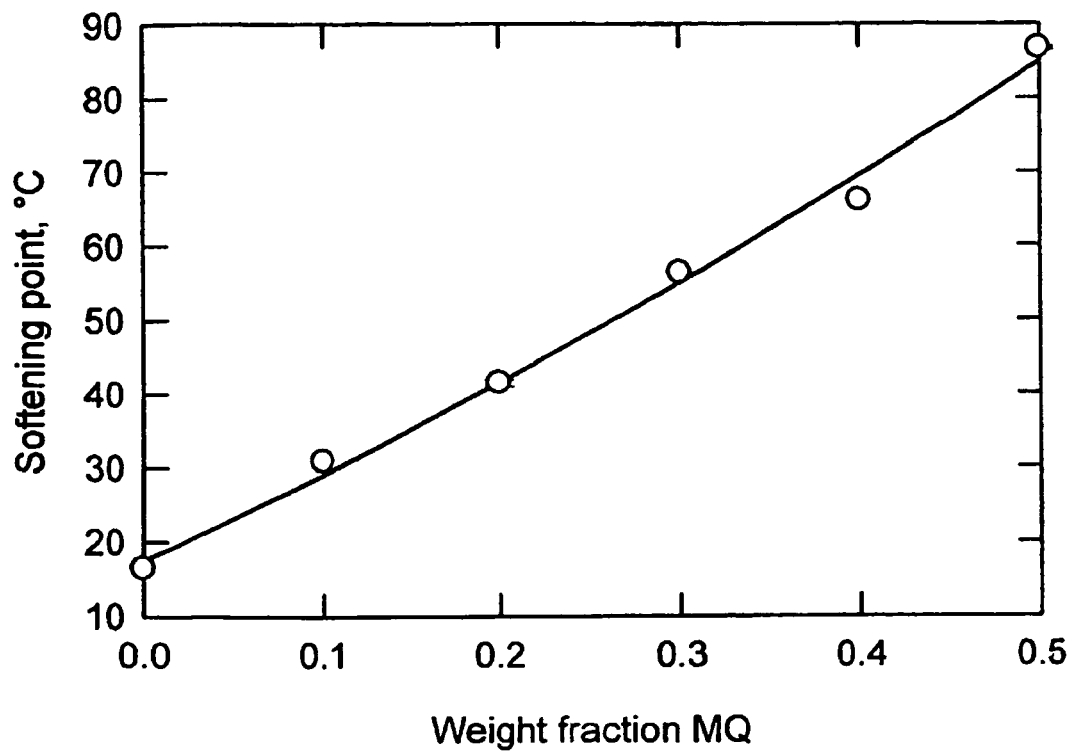
FIG. 2 shows the softening point of MQ/T(Pr) blends versus weight fraction MQ resin.

Rheology of MQ/T(Pr) blends showed a single softening point and steady change in softening temperature based on blend composition, as show in FIGS. 1 and 2 below.

Comparative Examples 7-19

MQ/DT(Me)/T(Pr) Resin Blend Comparisons

Solutions of MQ resins having various M:Q ratios of 0.75, 0.85, 0.95 (59.9, 73.3 and 70.8 wt % in xylenes respectively), a siloxane resin having the formula $D_{0.15}^{Me2}T_{0.85}^{Me}$ (50.3 wt % in toluene) was first prepared and then mixed with T propyl resin (75.5 wt % in toluene) were mixed. An aliquot of each mixture was poured into a 2-inch diameter aluminum weighing dish and heated in a forced air oven overnight at 105° C. followed by one hour and 30 minutes at 150° C. Qualitative visual observations of clarity, brittleness and hardness made are summarized in Table 2.

These examples demonstrate the immiscibility of MQ resins with the DT methyl with DT methyl resin/propylsilsesquioxane hydrolyzate resin blends.

TABLE 2

MQ/Methyl-T resin blends

| Example | M:Q Ratio of MQ Resin | MQ/DT(Me)/T(Pr) Blend Composition** | Clarity | Qualitative Brittleness |
|---|---|---|---|---|
| 7 | 0.75 | 10/90/0 | Hazy | Brittle |
| 8 | 0.75 | 25/75/0 | Hazy | Brittle |
| 9 | 0.75 | 50/50/0 | Hazy | Brittle |
| 10 | 0.85 | 10/90/0 | Hazy | Brittle |
| 11 | 0.85 | 25/75/0 | Hazy | Brittle |
| 12 | 0.85 | 50/50/0 | Hazy | Brittle |
| 13 | 0.95 | 10/90/0 | Hazy | Brittle |
| 14 | 0.95 | 25/75/0 | Hazy | Brittle |
| 15 | 0.95 | 50/50/0 | Hazy | Brittle |
| 16 |  | 0/50/50 | Hazy | Flexible |
| 17 |  | 0/75/25 | Hazy | Leathery |
| 18 | 0.85 | 25/25/50 | Hazy* | Brittle |
| 19 | 0.85 | 33/33/33 | Hazy* | Brittle |

*sample clear at 150° C. but becomes hazy on cooling to room temperature
**DT(Me) = $D_{0.15}^{Me2} T_{0.85}^{Me}$ resin and T(Pr) = $T_{1.0}^{Pr}$ hydrolyzate Example 20-25

MQ:$T^{pr}$ Blends in Personal Care Formulations

MQ resin, T-Propyl resin, and decamethylcyclopentasiloxane were mixed in a glass bottle by shaking and placing on a mixing wheel at the ratios indicated in Table 3 until homogeneous and uniform.

TABLE 3

Formulation of MQ:TPr blends

| Example # | Wt % MQ solids | Wt % $T^{Pr}$ solids |
|---|---|---|
| 20 | 100 | 0 |
| 21 | 0 | 100 |
| 22 | 85 | 15 |
| 23 | 50 | 50 |
| 24 | 15 | 85 |
| 25 | 30 | 70 |

Films resulting from the siloxane resins of Examples 20-25 were evaluated for gloss and tack at 35% solids in volatile solvent using a Leneta chart, evaluated in a foundation (color cosmetic) for durability, and as a hair fixative for curl retention and conditioning. The results are summarized in Table 4. The siloxane resins were applied to the hair tresses as 6 wt. % solutions in decamethylcyclopentasiloxane or isododecane carriers. Descriptions of the specific test methods and composition of the cosmetic formulation used in these evaluations follows Table 4.

TABLE 4

| Example # | 60° Gloss | Tack | Foundation Durability - ΔE (Change in color) | Curl Retention - Hair - % curl maintained after 5 hours at 95% RH |
|---|---|---|---|---|
| No Resin - neg control (exposed to carrier only) comparison | 55 | NA | 9.2 | 30.5-36.8, average to difficult to comb |
| 20 (comparative) | 34.8 | Not tacky | 3.8 | 53-58, Stiff rough, difficult to comb |
| 21 (comparative) | 78.4 | Very tacky | 11.0 | 44, Soft, sticky, easy to comb |
| 22 | 37.5 | Not tacky | 2.8 | 48.7, Slightly rough, slightly sticky, average combability |
| 23 | 44.6 | Yes, Less with time | 6.6 | 43.7, Slightly rough, slightly sticky, average combability |
| 24 | 62.8 | tacky |  | 43.4, Sticky, shiny, average combability |
| 25 |  |  | 8.3 |  |

Gloss Measurement:

1) Coat Leneta charts (Form N2C) with solution using a #8 Meyer rod
2) Allow chart to dry for 1 hour. Measure 60° gloss using a portable gloss meter at 3 points on the left ⅓ of the chart. Calculate the average of the 3 gloss values. Evaluate coating for tack, greasiness, fingerprint mark and if and how the coating rubs off the chart.
3) 4 hours after the drawdown was completed, measure 60° gloss using a portable gloss meter at 3 points on the middle ⅓ of the chart. Calculate the average of the 3 gloss values. Evaluate coating for tack, greasiness, fingerprint mark and if and how the coating rubs off the chart.
4) 24 hours after the drawdown was completed, measure 60° gloss using a portable gloss meter at 3 points on the right ⅓ of the chart. Calculate the average of the 3 gloss values. Evaluate coating for tack, greasiness, fingerprint mark and if and how the coating rubs off the chart.
5) Using the average gloss at the 3 different times, calculate the overall average.

Curl Retention Test Method

Materials

Prepared natural virgin brown hair tresses or oriental hair of 2 g, 25 cm.

Comb Trade Mark: Ace;.

Humidity chamber to regulate temperature and humidity during test.

Procedure for Pre-Treating the Swatches (Washing):

1) Wet 5 tresses for 30 sec with tap water at 37° C.
2) Lather the 5 tresses for 30 sec. With 5 g of the 30% SLS solution (Empicol LX28/Albright & Wilson), stroking the tresses downward ensure you repeat the same movement for all the hair washed. Leave on hair for 30 sec.
3) Rinse the tresses for 1 minute with tap water at 37° C.
4) Remove the excess of water by running the tresses between the two fingers 3 times.
5) Allow the tresses to dry overnight on a paper towel at room temperature.

Procedure for Treating the Swatches with the Resin and Curling:

Blank or negative control is the solvent used in the treatments.
1) Dip 1 tress at a time 3 times in 37° C. tap water and remove excess of water by stroking the tress between 2 fingers
2) Lay the tress down on a clean support and apply 100 microliters of a 6% resins solution all along the using a calibrated micropipette
3) Detangle the tress completely
4) Roll the tress on rod spiral curler,
5) Leave the swatches to dry overnight in an oven at 40° C.

Test—Curl Retention Measurements:
1. Start the humidity chamber 2 hours before the test set at 70% humidity and 25 C.
2. Carefully remove the roller from hair by twisting it slightly, 10 minutes before the start of the test. Cut the ends of the tress in order to make it even (cut as few as possible).
3. Ensure each tress is correctly curled.
4. Hang the tresses in the humidity chamber: the bottom of the wax sealing on the tress should be on the line "0" of the millimeter paper sheet in the back of the chamber.
5. Measure hair tress length at predetermined intervals of time, the length is measured as the distance between the bottom of the wax sealing and the bottom of the tress—be aware that the bottom of the tress is going down, so the view angle is perpendicular to the glass.
6. After the 5 hours, remove the tresses from the humidity chamber and measure the tress length at its maximum, by unrolling it completely. Calculate curl retention as described below.

Percent curl retention is calculated as follows:

$$\% \text{ Curl Retention} = \frac{\text{max length} - \text{length at } T = x}{\text{max length} - \text{length at } T = 0} \times 100$$

Foundation Formulation

Pigment Premix:
50 wt % DC 245 Fluid
13.16 wt % Carde AS Titanium dioxide (caprylyl silane treated)
11.41 wt % Carde AS Red Iron Oxide(caprylyl silane treated)
18.26 wt % Carde AS Yellow Iron Oxide(caprylyl silane treated)
7.17 wt % Carde AS Black Iron Oxide(caprylyl silane treated)

Procedure:
1) Place DC 245 fluid in Waring Blender
2) Add titanium dioxide and mix by pressing the pulse button for 2 seconds for 15 seconds total.
3) Add red iron oxide and mix the same as titanium dioxide
4) Continue with the other pigments
5) When all materials have been dispersed, mix on high and shred for 30 sec to grind the pigments
6) Place premix into a round glass jar and place on pail roller for 6 hours.

Phase A
20.50 wt % Pigment Premix
7.50 wt % DC 5225C
8 wt % of a 50% resin solids in solvent Phase B
54.80 wt % DI Water
1.0 wt % NaCl
0.20 wt % Polysorbate 20

Procedure for Liquid Water in Oil Foundation
1) Put pigment dispersion on roller for 1 hour.
2) Weigh out resin and solvent to make a 50% solids dilution. Use oven and wheel to mix
3) Combine ingredients in Phase A, mix until uniform using a dual blade, turbulent style mixing action.
4) Combine ingredients in Phase B in separate beaker, mix until uniform using a magnetic stirrer
5) Increase mixing speed of Phase A to 1376 rpm and very slowly add Phase B through an addition funnel. This addition should take 10 mins.
Continue mixing for an additional 10 min.

Foundation Durability Method: Gardner Abrasion Tester
1) Cut collagen into 3.5"×3" pieces, place one on each of the 3"×2.5" polycarbonate blocks and put in the humidity chamber overnight. This chamber must be at a constant 98% relative humidity level.
2) Remove collagen and block from chamber. Secure collagen to block with Scotch tape taking care not to place any tape on the top of the block's surface.
3) Add approximately 1 gram of foundation to the collagen, beading it across the top of the block. Using a #8 Meyer rod, coat the collagen with the foundation by placing the rod on the bead of foundation and spreading it downward to the bottom of the block. The final coating weight should be approximately 0.2 grams. This operation may need to be repeated to obtain the proper coating weight. Remove any material from the sides of the block.
4) Allow sample on collagen to dry. Drying times vary with different samples. Entire sample must be free from any wetness before testing. Measure color of sample on collagen for the initial baseline color using a spectrophometer or calorimeter. L*, a*, and b* designate the place of the colored object in a tri-dimensional space.
5) Place block with collagen face-up on the Gardner Abrasion Tester making sure that the block is in the tester. The soft side of Velcro is attached to the insult block to abrade or insult the foundation sample on the collagen. The insult block rubs back and forth across the foundation sample. One insult consists of one back and forth motion. Insult the foundation sample on the collagen 20 times. The machine can be stopped at certain intervals to measure the color.
6) After the foundation sample is insulted 20 times, the color is read as L*, a*, b* and the change in color, ΔE, is calculated (see equation below). The number of insults, coating weight, and repetitions can be changed to fit the needs of the material being tested. This is up to the discretion of the operator.

$$\Delta L^*, \Delta a^* \text{ and } \Delta b^* = \begin{matrix} \text{value after abrasion} - \\ \text{value at initial baseline before abrasion.} \end{matrix}$$

$$\Delta E = \left(\Delta L^2 + \Delta a^{*2} + \Delta b^{*2}\right)^{1/2}$$

With larger ΔE's, more foundation was removed and therefore the foundation is less durable.

The invention claimed is:
1. A siloxane resin composition obtained by mixing:
A) a MQ resin comprising at least 80 mole % of siloxy units selected from

$(R^1{}_3SiO_{1/2})_a$ and $(SiO_{4/2})_b$ units, where $R^1$ is independently an alkyl group having from 1 to 8 carbon atoms, an aryl group, a carbinol group, or an amino group, with the proviso that at least 95 mole % of the $R^1$ groups are alkyl groups, a and b has a value greater than zero, and the ratio of a/b is 0.5 to 1.5;

B) a propyl silsesquioxane resin comprising at least 80 mole % $R^3SiO_{3/2}$ units, where $R^3$ is independently an alkyl group having from 1 to 8 carbon atoms, an aryl group, a carbinol group, or an amino group, with the proviso that at least 40 mole % of the $R^3$ groups are propyl, and optionally;

C) a volatile siloxane or organic solvent, wherein the weight ratio of component A to B is from 90:10 to 10:90.

2. A personal care product comprising the siloxane resin composition of claim 1.

3. The personal care product of claim 2, where the personal care product is a cosmetic product.

4. The personal care product of claim 2, where the personal care product is a hair care product.

5. The silicone resin composition of claim 1 wherein the weight ratio of component A to B is from 85:15 to 15:85.

* * * * *